Figure 2:
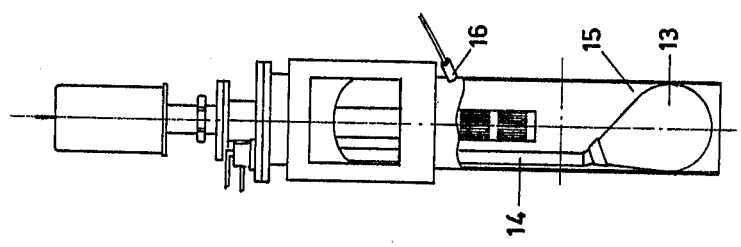

United States Patent [19]

Hemmings

[11] 4,151,744
[45] May 1, 1979

[54] METHOD AND APPARATUS FOR THE MEASUREMENT AND CONTROL OF VISCOSITY OF SLURRIES

[75] Inventor: Charles E. Hemmings, North Ryde, Australia

[73] Assignee: M.D. Research Company Pty. Limited, New South Wales, Australia

[21] Appl. No.: 867,052

[22] Filed: Jan. 5, 1978

[30] Foreign Application Priority Data

Jan. 17, 1977 [AU] Australia .............................. PC8761

[51] Int. Cl.² ........................................... G01N 11/00
[52] U.S. Cl. ........................................... 73/54; 137/4
[58] Field of Search ............... 73/54, 61 R, 53; 137/4, 137/92

[56] References Cited

U.S. PATENT DOCUMENTS

| | | | |
|---|---|---|---|
| 3,017,767 | 1/1962 | Mossberg | 73/54 |
| 3,163,172 | 12/1964 | Buzzard | 73/54 X |
| 3,473,367 | 10/1969 | Troland et al. | 73/54 |

Primary Examiner—Richard C. Queisser
Assistant Examiner—Joseph W. Roskos
Attorney, Agent, or Firm—Ladas, Parry, Von Gehr, Goldsmith & Deschamps

[57] ABSTRACT

A new and improved method and apparatus for the measurement and control of the bulk properties of slurries is provided. The bulk properties are measured in the slurry while it is flowing downwards at a rate greater than the settling velocity of the discontinuous phase of the slurry.

14 Claims, 4 Drawing Figures

METHOD AND APPARATUS FOR THE MEASUREMENT AND CONTROL OF VISCOSITY OF SLURRIES

This invention relates to an improved method and apparatus for the measurement and control of the bulk properties of slurries.

The term "slurry" as used throughout this specification means a material which does not appreciably resist deformation—that is it has fluid-like properties—and which is composed of at least two distinguishable components of which one is fluid forming a continuous phase and in which at least one other component forms a discontinuous phase.

The term "settling slurry" as used throughout this specification means a slurry in which the discontinuous phase rapidly settles under gravity causing segregation and non uniform distribution of the slurry phases unless continuously and vigorously mixed or agitated. The slurry discharge of a closed circuit grinding mill is a typical example of a settling slurry.

The term "bulk property" as used throughout this specification means a property of a slurry or a settling slurry such as viscosity or density, when measured under conditions which promote substantial homogeneity, that is, when the dispersed phase is uniformly distributed throughout the continuous phase.

The term "viscosity" as used throughout this specification means apparent viscosity since for the slurries to which this invention applies the shear stress is not in general directly proportional to the shear rate. For such substances apparent viscosity is the slope of the tangent to the shear stress/shear rate curve at the values at which measurement is made.

The principal object of the invention is to provide a method and apparatus for the continuous measurement of the bulk properties of a settling slurry. Such measurement is, with the methods and apparatus currently in use or available for use, so difficult to achieve that measurement of bulk properties such as for instance viscosity, is seldom used to monitor such property and less often still to control it despite the significant cost and quality control advantages that such measurement and control can confer on processes involving for instance grinding mill slurries. A characteristic of such slurries is the wide size range of the solid particles they contain with consequent problems in the prevention of selective settlement and segregation of the coarser particles in, around and away from the sensing apparatus of the measuring device and the consequent malfunction of the apparatus or at best results not representative of the bulk property being measured. This invention overcomes such problems and is therefore particularly applicable to the measurement of the bulk properties of grinding mill slurry.

The provision of headroom for measuring and control apparatus is usually costly and often inconvenient to provide, particularly for large and heavy machinery installations such as grinding mills, and it is an object of this invention to provide a compact system for use in such installations which requires minimum headroom and is adapted to conform to the machines serviced.

Settling slurries are usually very abrasive, particularly if the slurry velocity is greater than a few feet per second, and can cause heavy wear of vessels and equipment in contact with it. It is therefore an object of this invention to provide a robust measuring system in which the slurry velocities are of a low order.

In measuring the bulk properties of slurries for control purposed it is important that the time interval between slurry production and slurry property measurement be minimal. This invention achieves this requirement by a configuration of apparatus which allows close coupling to any production unit preceding it and has a very small retention volume and consequently low residence time for the passage of the slurry.

The improved method and apparatus provided by this invention to achieve the foregoing objectives include flowing the slurry downwards through a pipe or conduit of such cross sectional area relative to the slurry flow rate that the vertical components of the slurry phase velocities are significantly greater than the settling velocity of the continuous phase of the slurry; providing at the lower extremity of said pipe or conduit flow rate controlling means so that at all cross sections the pipe or conduit is always completely occupied by slurry, measuring by any means one or more of the bulk properties of the slurry within a region of said downwardly flowing slurry, transmitting by any means signals from said measuring means, displaying and/or recording said signals and/or employing such signals manually or automatically to control the means by which the slurry properties are determined or modified.

The relevance of the requirement that the vertically downward component of slurry velocity in the region of measurement should be significantly greater than the settling velocity of the discontinuous phase is that the slurry will be substantially homogeneous in the said region of measurement, the composition of said slurry in the said zone of measurement being substantially that of the composition of slurry entering and leaving the measuring zone. This may be demonstrated algebraically as follows:

$V_s$ = Mean vertically downward velocity of the discontinuous phase.

$V_w$ = Mean vertically downward velocity of the water.

$V_f$ = Mean velocity of fall of the discontinuous phase relative to water = $V_2 - V_w$.

$C_m$ = Concentration by volume of the discontinuous phase in the measuring region.

$A_s$ = Mean cross sectional area of the measuring region occupied by the discontinuous phase.

$A_w$ = Mean cross sectional area occupied by the water.

$r_m$ = Volume ratio of discontinuous phase to water in the measuring region so that $r_m = C_m/1 - C_m$ and let - r = Volume ratio of the discontinuous phase to water in proportion to the rate at which it enters and leaves the system.

Then

Volume flow rate of discontinuous phase = $V_s A_s$

Volume flow rate of water = $V_w A_w$ and $$\frac{V_s A_s}{V_w A_w} = r; \frac{A_s}{A_w} = \frac{V_w}{V_s} \cdot r = \frac{V_w}{V_w + V_f} \cdot r$$

Also

-continued
$$\frac{A_s}{A_w} = \frac{C_m}{1 - C_m} = r_m$$
so that
$$r_m = \frac{V_w}{V_w + V_f} \cdot r$$
and
$$r_m \longrightarrow r \text{ when } V_w >> V_f$$

In practice $V_w$ can readily be 50 times as great as $V_f$ so that $r_m$ may readily approach to within 2% of r.

Figure 1:
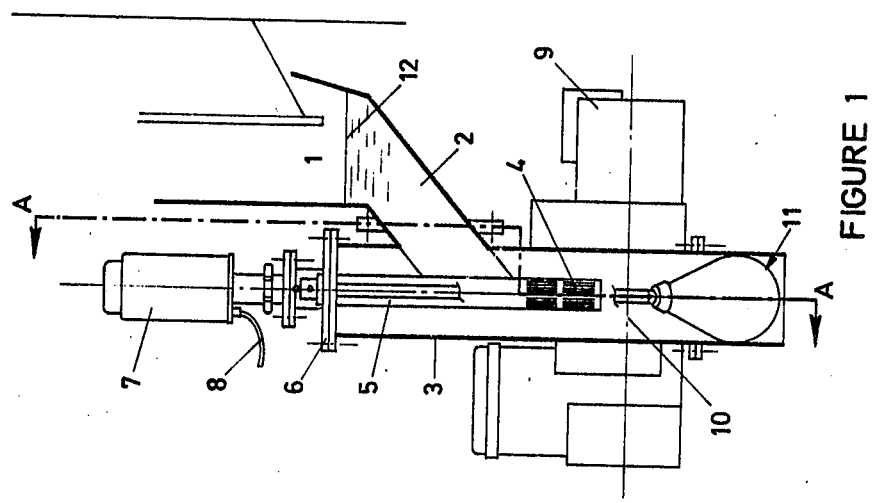

The method of operation and the apparatus of the invention may best be described by reference to the accompanying drawings wherein FIG. 1 is a cross sectional elevation of the apparatus arranged for sensing and measuring the viscosity and density of slurry discharged from a grinding mill.

FIG. 2 is a sectional elevation on the line "AA" of FIG. 1.

Figure 3:
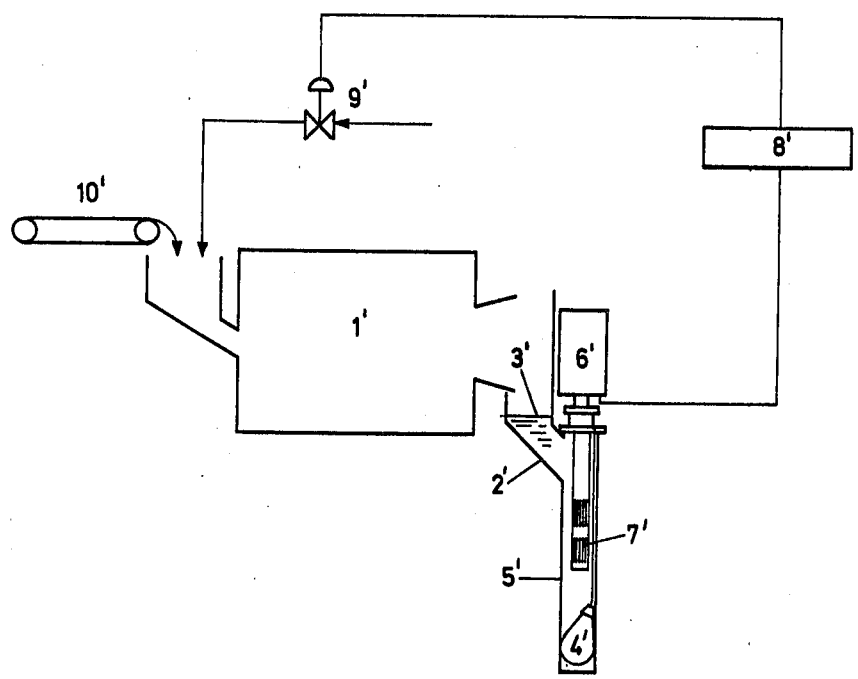
Figure 4:
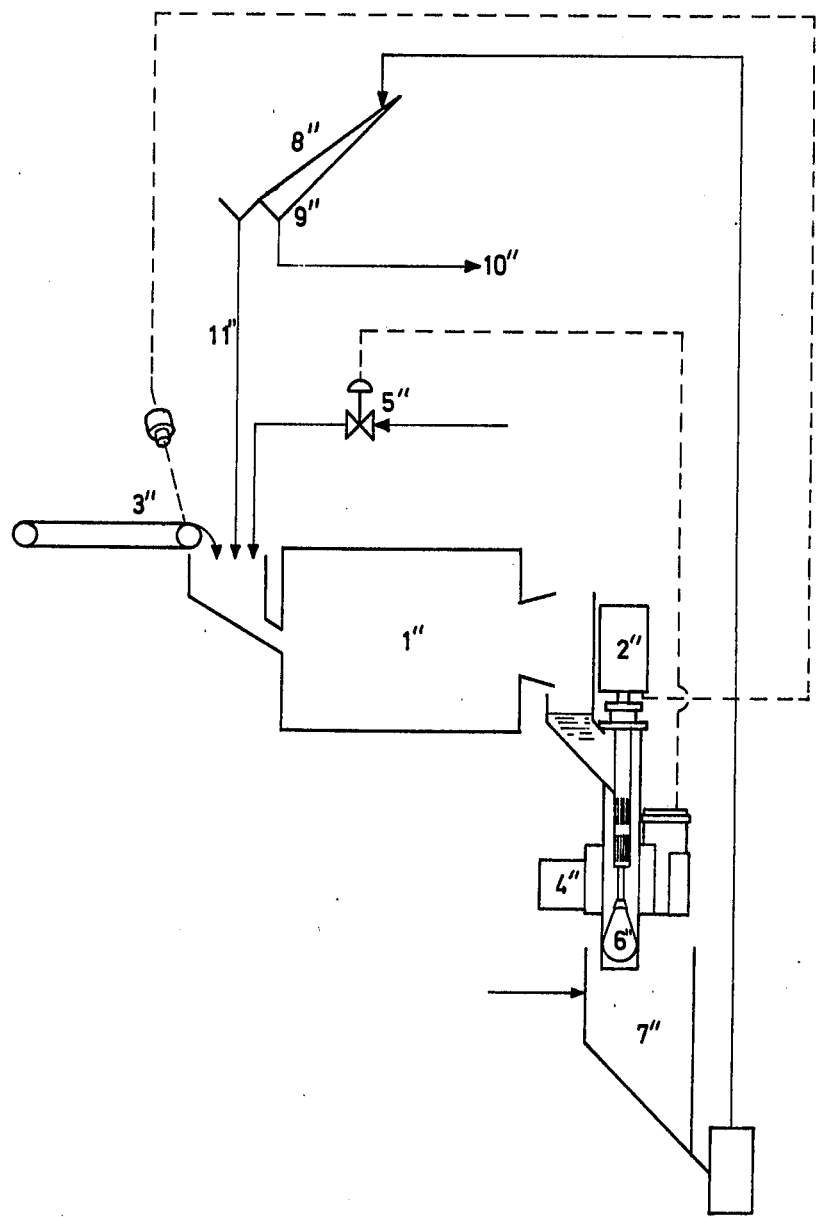

FIG. 3 shows diagrammatically the apparatus applied to control automatically the viscosity of the slurry discharged by an open circuit grinding mill, and FIG. 4 shows diagrammatically the apparatus applied to the automatic control of the operation of a closed circuit grinding mill by measuring both the viscosity and density of the mill discharge slurry and employing the signals from such measurements to control mill feed rate and water addition.

Referring to FIGS. 1 and 2 the slurry from the mill discharge hopper 1 is directed by attached flanged sloping inlet connection 2 of the apparatus to the vertical pipe, conduit or column 3. Situated adjacent below the sloping inlet connection 2 and symmetrically in the said vertical column 3 is the sensing element 4 of a viscometer which further comprises an element support tube 5 housing mechanical transmitting means and passing through a flange-sealed opening in flange 6 which terminates and seals the upper end of column 3. The viscometer measuring head 7 which attaches to the upper end of housing 5 converts the mechanical signal related to the slurry viscosity from the sensing element 4 to an electrical signal which may be transmitted by output cable 8 to any convenient location for display, recording and/or control. Slurry flows uniformly downwards around the viscometer sensing element 4 within a velocity range predetermined by relating the cross sectional area of column 3 to the range of the slurry flow rate over which measurement of bulk properties is desired.

Immediately below the viscometer sensing element 4 is the nuclear density gauge 9 mounted on the outside of column 3 and arranged to pass a sensing gamma ray beam centrally through the slurry stream and centred on the horizontal line 10 downwardly clear of the viscometer sensing element 4. The nuclear density gauge 9 provides an electrical output signal related to the bulk density of the downwardly flow slurry through which the gamma ray beam passes, said signal being available together with the viscometer signal for display, recording and/or control.

Adjacent below and clear of the gamma ray beam of the nuclear density gauge 9 is a flow control valve 11 adjusted to regulate the rate at which slurry is discharged from column 3 and to match this rate to that at which slurry enters the column from the grinding mill so that the upper free surface 12 of the slurry is maintained above the top of sloping inlet connection 2 and that all cross sections of column 3 are at all times completely occupied with downwardly flowing slurry. Whilst any suitable means may be used for such column flow control the pneumatic sac type flow control valve 11 depicted is particularly united to the control of settling slurry of the grinding mill type the density of which may be typically 50% solids by volume with a significant fraction of particles larger than 5 millimeters and which cause blockage and malfunction of flow control valves not specially designed for this duty. Flow control valve 11 comprises an air inflated sac 13 supported from flange 6 by air pipe connection 14 and capable of exerting sealing contact with column 3 or, under reduced air pressure, of providing an area as at 15 between the sac and the column to permit the out-flow of slurry, said reduced air pressure being regulated by any suitable controller actuated from a slurry pressure tapping as at 16 in the column 3 to maintain the free slurry surface 12 at a constant height above said pressure tapping.

The arrangement just described defines a downwardly elongated region in the vertical column 3, extending above the flow control valve 11 to immediately below the sloping inlet connection 2, in which the slurry is homogenous and its bulk properties may accurately be measured.

As will be apparent from FIG. 1 the configuration of the apparatus above described is such as to require minimum headroom when installed in the manner shown for the measurement of grinding mill discharge properties. A further advantage of the arrangement depicted is that all the apparatus immersed in the slurry is attached to flange 6 and may be removed with it for maintenance without interrupting the slurry flow or the operation of the grinding mill.

The diagram of FIG. 3 shows the invention applied to the control of a grinding mill operating in open circuit and arranged for the measurement of viscosity only. Slurry from the mill 1' is collected by hopper 2' in which a free slurry surface is maintained at 3' by sac control valve 4' in the manner described for FIG. 1'. The viscosity of the slurry flowing downwardly in column 5' is measured by viscometer 6' through sensing element 7' and a signal related to the pulp viscosity is employed by controller 8' to regulate through valve 9' the water supply to the grinding mill, the solids feed to which is regulated by feeder 10. The action of the viscometer control circuit is to maintain constant viscosity of mill discharge slurry by increase or decrease of the supply of water to the mill according as the viscosity of the mill discharge slurry tends to increase or decrease respectively due to causes such as changes in solids feed rate, sizing, grindability or moisture content.

The diagram of FIG. 4 illustrates the application of the invention to the control of a grinding mill operating in closed circuit with a sizing device and arranged for the measurement of both viscosity and density. For this application the arrangement of the apparatus of the invention is as illustrated and described with reference to FIG. 1. For control of the operation of the grinding mill 1" the signal from the viscometer 2" is applied to regulate the new feed rate of solids to the mill via feeder 3" and the signal from the nuclear density gauge 4" is applied to regulate through valve 5" the water supply to the mill. Slurry discharging past the flow control valve 6" is received and diluted with water in hopper 7" and pumped to sizing screen 8" the undersize 9" from which is finished product 10" and the oversize 11" from which joins the new feed and returns to the grinding mill.

When a grinding mill is operated in closed circuit with a sizing device as above described stable operation at optimum efficiency becomes critically dependent on the close control of both slurry viscosity and slurry density at predetermined values and the use of the invention in the manner above described facilities such close control.

Whilst in most applications it would be usual to measure and/or control slurry properties continuously it should be noted that the invention may be practised by generating and/or using the measurement signals intermittently.

Whilst the principal object of this invention is to provide a method and apparatus for the continuous measurement and control of a settling slurry it can nonetheless be used advantageously for similar purposes with slurries in which settlement, segregation and non uniform distribution of the discontinuous phase are of lesser consequence.

As the invention may be embodied in several forms without departing from its essential character, the embodiments and applications presented are intended to be illustrative and not restrictive.

What I claim is:

1. A method for the measurement of the bulk properties of a slurry comprising flowing the slurry downwards through a pipe or conduit of such cross sectional area relative to the slurry flow rate that the vertical components of the slurry phase velocities are significantly greater than the settling velocity of the discontinuous phase of the slurry; providing at the lower extremity of said pipe or conduit flowrate controlling means so that at all cross sections the pipe or conduit is always completely occupied by slurry, measuring one or more of the bulk properties of the slurry within a region of said downwardly flow slurry and transmitting signals from said measuring means related to the bulk properties measured and displaying and/or recording said signals.

2. A method for the control of the bulk properties of a slurry comprising employing signals related to said properties derived according to the method of claim 1 to control automatically the means by which the slurry properties are determined or modified.

3. A method for the control of the bulk properties of a slurry comprising employing signals related to said properties derived according to the method of claim 1 to control manually the means by which the slurry properties are determined or modified.

4. Apparatus for the measurement of the bulk properties of a slurry according to the method of claim 1 characterized by a substantially vertical conduit having an inlet at its upper end connectable to a feed hopper; a flow control valve at its lower end; and measuring means located within or adjacent to said conduit to measure the bulk properties of the slurry which flows between said hopper and said valve.

5. Apparatus according to claim 4 characterized in that said measuring means measures more than one bulk property.

6. Apparatus according to claim 4 characterized in that said measuring means comprises a viscometer.

7. Apparatus accoridng to claim 4 characterized in that said measuring means comprises a sensing device for slurry density.

8. Apparatus according to claim 4 characterized in that the flow control valve is in the form of an inflatable sac capable, when inflated, of exerting sealing contact with the interior of said conduit or, capable under partial inflation of providing a limited cross-sectional area between said sac and said conduit to permit the outflow of the slurry from said conduit to be controlled by means of a control fluid communicating with the interior of said sac.

9. Apparatus according to claim 4 characterized in that a pressure tapping is located adjacent to said measuring means in said conduit, said tapping controlling said flow valve.

10. Apparatus according to claim 4 characterized in that said measuring means is connected to a controller which regulates supply of slurry to said conduit in volumes depending on the bulk property of the slurry measured by said measuring means.

11. Apparatus according to claim 4 characterized in that the apparatus is in combination with a slurry producing unit operating in closed circuit and also characterized in that said viscometer regulates feed of solids to said slurry producing unit and said density gauge regulates supply of water to said slurry producing unit.

12. Apparatus according to claim 8 characterized in that a pressure tapping is located adjacent said measuring means in said conduit, said tapping controlling said flow control valve.

13. Apparatus according to claim 8 characterized in that said measuring means is connected to a controller which regulates supply of slurry to said conduit in volumes depending on the bulk property of the slurry measured by said measuring means.

14. Apparatus according to claim 8 characterized in that the apparatus is in combination with a slurry producing unit operating in closed circuit and also characterized in that said viscometer regulates feed of solids to said slurry producing unit and said density gauge regulates supply of water to said slurry producing unit.

* * * * *